US010004514B2

(12) United States Patent
Ladjali (10) Patent No.: US 10,004,514 B2
(45) Date of Patent: Jun. 26, 2018

(54) BODILY TISSUE TREATMENT KIT

(71) Applicant: Mustapha Ladjali, Sannois (FR)

(72) Inventor: Mustapha Ladjali, Sannois (FR)

( * ) Notice: Subject to any disclaimer, the term of this patent is extended or adjusted under 35 U.S.C. 154(b) by 394 days.

(21) Appl. No.: 14/761,683

(22) PCT Filed: Jan. 17, 2014

(86) PCT No.: PCT/EP2014/050915
§ 371 (c)(1),
(2) Date: Oct. 12, 2015

(87) PCT Pub. No.: WO2014/111531
PCT Pub. Date: Jul. 24, 2014

(65) Prior Publication Data
US 2016/0038149 A1    Feb. 11, 2016

(30) Foreign Application Priority Data
Jan. 18, 2013   (FR) ..................................... 13 50462

(51) Int. Cl.
*A61B 17/122* (2006.01)
*A61B 17/128* (2006.01)
(Continued)

(52) U.S. Cl.
CPC .... *A61B 17/1227* (2013.01); *A61B 17/00234* (2013.01); *A61B 17/1285* (2013.01);
(Continued)

(58) Field of Classification Search
CPC .......... A61B 17/1227; A61B 17/00234; A61B 17/1285; A61B 2017/00783;
(Continued)

(56) References Cited

U.S. PATENT DOCUMENTS 5,478,353 A * 12/1995 Yoon ................... A61B 17/0057
606/104
7,635,329 B2 * 12/2009 Goldfarb ............ A61B 17/0401
600/37

(Continued)

FOREIGN PATENT DOCUMENTS

| EP | 1312314 A1 | 5/2003 |
|---|---|---|
| GB | 2161206 A | 1/1986 |
| WO | 2006/039199 A2 | 4/2006 |
| WO | 2006/098994 A1 | 9/2006 |

OTHER PUBLICATIONS

French Search Report dated Sep. 30, 2013 issued in corresponding French Patent Application No. 1350462.
(Continued)

*Primary Examiner* — Julian W Woo
(74) *Attorney, Agent, or Firm* — Troutman Sanders LLP (57) ABSTRACT

The invention relates to a clamp for treating a bodily tissue having a prolapse, the clamp including a body and at least two flexible arms for clamping the prolapse protruding with respect to the body, each clamping arm comprising a proximal end connected to the body and a free distal end opposite to the proximal end. The clamp includes at least one flexible member for crushing the prolapse, the crushing member protruding from the body or from one of the arms.

20 Claims, 7 Drawing Sheets

(51) Int. Cl.
*A61F 2/24* (2006.01)
*A61B 17/00* (2006.01)
(52) U.S. Cl.
CPC ........................ *A61F 2/2463* (2013.01); *A61B 2017/00243* (2013.01); *A61B 2017/00349* (2013.01); *A61B 2017/00783* (2013.01)
(58) Field of Classification Search
CPC ........... A61B 2017/00349; A61B 2017/00243; A61F 2/2463
See application file for complete search history.

(56) References Cited

U.S. PATENT DOCUMENTS

| | | |
|---|---|---|
| 2004/0220593 A1 | 11/2004 | Greenhalgh |
| 2012/0330407 A1 | 12/2012 | Dale et al. |
| 2013/0023723 A1 | 1/2013 | Mittal et al. |
| 2013/0153626 A1 | 6/2013 | Felder et al. |
| 2014/0039608 A1* | 2/2014 | Eidenschink ......... A61F 2/2427 623/2.11 |

OTHER PUBLICATIONS

International Search Report and Written Opinion dated Apr. 15, 2014 issued in corresponding PCT Patent Application No. PCT/EP2014/050915.

* cited by examiner

BODILY TISSUE TREATMENT KIT

CROSS REFERENCE TO RELATED APPLICATIONS

This application is the U.S. National Phase of International Patent Application Serial No. PCT/EP2014/050915, filed on Jan. 17, 2014, which claims priority to French Patent Application No. 13 50462, filed on Jan. 18, 2013.

FIELD OF THE INVENTION

The present invention relates to a clamp for treating a bodily tissue having a prolapse, the clamp including a body and at least two flexible arms for clamping the prolapse protruding with respect to the body, each clamping arm comprising a proximal end connected to the body and a free distal end opposite to the proximal end.

BACKGROUND OF THE INVENTION

This clamp is notably applied to the treatment of heart valves, and in particular to the treatment of mitral valves.

A mitral valve typically consists of two leaflets, both anterior and posterior, and controls the blood flow which flows from the left auricle to the left ventricle of the heart. The mitral valve ensures one-way circulation of the blood flow, avoiding blood backflow at the end of the ventricular contraction.

In order to avoid blood backflow, the leaflets of the valve should ensure coaptation through their free edges.

In the case of prolapse, i.e. release of the wall of the leaflet, one of the leaflets has a bulge which defines a thickened and surface-increased protruding area. The prolapse may then prevent the valve from closing sealably. The result of this is mitral insufficiency, i.e. a backflow of the blood into the left auricle when the ventricle contracts.

A possible treatment of this disease consists in surgical ablation of the prolapse. However, such an invasive operation is tedious and has non-negligible risks for the patient, notably when the patient is old and/or with poor health.

In order to overcome this problem, another means known for treating this disease in an endovascular way consists of placing a clip intended to form a connection point between the anterior leaflet and the posterior leaflet, at the prolapse. This allows restoration of coaptation between the leaflets of the valve at the prolapse.

However, the clip forms a permanent connection point between the leaflets of the valve. Thus, upon opening of the valve, the leaflets only open on either side of the connection point creating two distinct passage apertures. The blood then flows through two separate routes from each other through the connection point.

This type of treatment suppresses the problem at the prolapse. However, it does not give entire satisfaction, since it perturbs the coaptation of the leaflets away from the prolapse, and since it perturbs the passing of the blood at the valve.

SUMMARY OF THE INVENTION

One object of the invention is therefore to obtain a clamp for treating a tissue having a prolapse giving the possibility of treating the prolapse in a not very invasive way, by perturbing as less as possible the tissue once the clamp is set into place.

In particular, when the tissue is a heart valve leaflet, an object of the invention is to treat the prolapse by allowing the valve to close sealably when the ventricle contracts, and ensuring satisfactory coaptation of the leaflets.

For this purpose, the object of the invention is a clamp for treating a bodily tissue having a prolapse characterized in that it includes at least one flexible member for crushing the prolapse, the crushing member protruding from the body facing the flexible arms between an end bound to the body and a free end.

The treatment kit according to the invention may comprise one or more of the following features, taken individually or according to any technically possible combination:

both clamping arms are deformable between a closed rest configuration in which the distal ends of both clamping arms are brought closer to each other, and an open separation configuration in which the distal ends of both clamping arms are spaced apart from each other, the crushing member being movable with respect to the arms between a position for inserting the prolapse away from the arms and a position for crushing the prolapse brought closer to the arms, the crushing member being advantageously elastically urged towards the closer position;

each arm is movable with respect to the other arm along a separation direction between the closed configuration and the open configuration, the free end of the crushing member being movable substantially perpendicularly with respect to each separation direction between the insertion position and the crushing position;

each arm is movable with respect to the other arm along a separation direction between the closed configuration and the open configuration, the free end of the crushing member being movable parallel to at least one separation direction between the insertion position and the crushing position;

the clamp comprises a member for deforming the clamping arms borne by the body, the member for deforming the clamping arms being connected to both clamping arms and being able to be actuated for deforming both clamping arms between the closed rest position and the open separation configuration;

the member for deforming the clamping arms is formed with a wire connected to both clamping arms, the wire being maintained with respect to the body in at least one guidance point and advantageously extending partly along the circumference of the body;

each clamping arm comprises a surface for side clamping the prolapse, each clamping surface extending facing each other and comprising at least one protruding portion and at least one mating recessed portion respectively;

the crushing member includes a blade having an internal surface for crushing the prolapse extending substantially perpendicularly to the side clamping surface of each clamping arm.

the body, both clamping arms and the crushing member are made in one piece and made together in the same material;

The object of the invention is also a kit for treating a bodily tissue having a prolapse, comprising:

a clamp; and a stent rod extending along a main axis and defining at least one aperture for retaining the clamp.

The treatment kit according to the invention may comprise one or several of the following features, taken individually or according to any technically possible combination:
- the stent rod includes an internal maintaining surface able to maintain the fixed body in rotation with respect to the main axis;
- the treatment kit comprises a movable maneuvering member relatively to the stent rod in order to maneuver the crushing member between the insertion position of the prolapse and the position for crushing the prolapse;
- the stent rod comprises a first compartment and a second compartment, the first and second compartments extending along the main axis, the first compartment retaining the clamp, the second compartment containing the movable maneuvering member.

The object of the invention is also a treatment kit according to any of claims 1 to 15.

In an embodiment, the kit is without any flexible member for crushing the prolapse, the crushing member protruding from the body facing the arms between an end bound to the body and a free end.

The invention further relates to a method for treating a bodily tissue having a prolapse, comprising the steps:
- providing a treatment kit as defined above, the clamping arms occupying a rest configuration;
- deforming the clamping arms to a separation configuration, positioning the distal ends of the clamping arms around the prolapse;
- capturing a free edge of the prolapse by means of the capture and displacement mechanism;
- pulling the free edge via the capture and displacement mechanism in order to bring the prolapse between the side clamping surfaces;
- deforming the clamping arms to a rest configuration so as to clamp the prolapse.

Advantageously, the traction of the free end includes lifting the free edge of the prolapse transversely with respect to the axis of the clamp, the movement being guided by the capture and displacement mechanism.

The treatment method according to the invention may further comprise the feature according to which the bodily tissue is a valve leaflet, advantageously a mitral valve leaflet.

BRIEF DESCRIPTION OF THE DRAWINGS

The invention will be better understood upon reading the description which follows, only given as an example and made with reference to the appended drawings wherein.

DETAILED DESCRIPTION OF THE INVENTION

In all the following, the terms of «proximal» and «distal» are respectively meant as relatively closer to the operator, and as relatively farther away from the operator.

Figure 4:
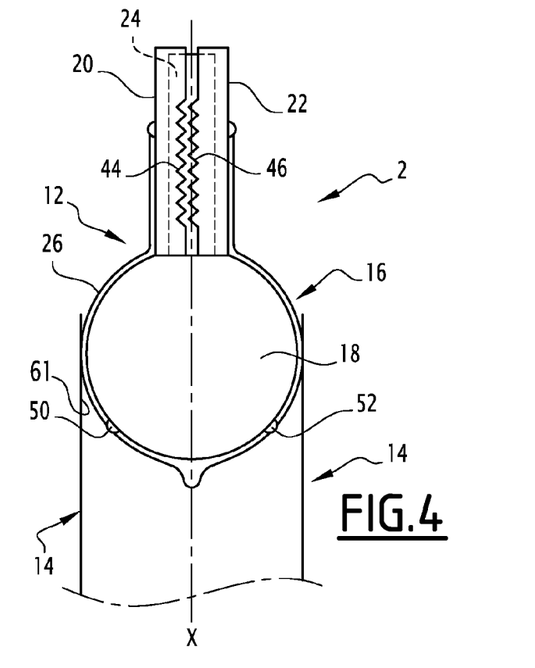
FIG. 4 is a schematic illustration of a treatment kit according to the invention.

A treatment kit 2 according to the invention is illustrated in FIG. 4.

This treatment kit 2 is intended for treating a bodily tissue having a prolapse, notably for the treatment of a heart valve such as a mitral valve.

Figure 1:
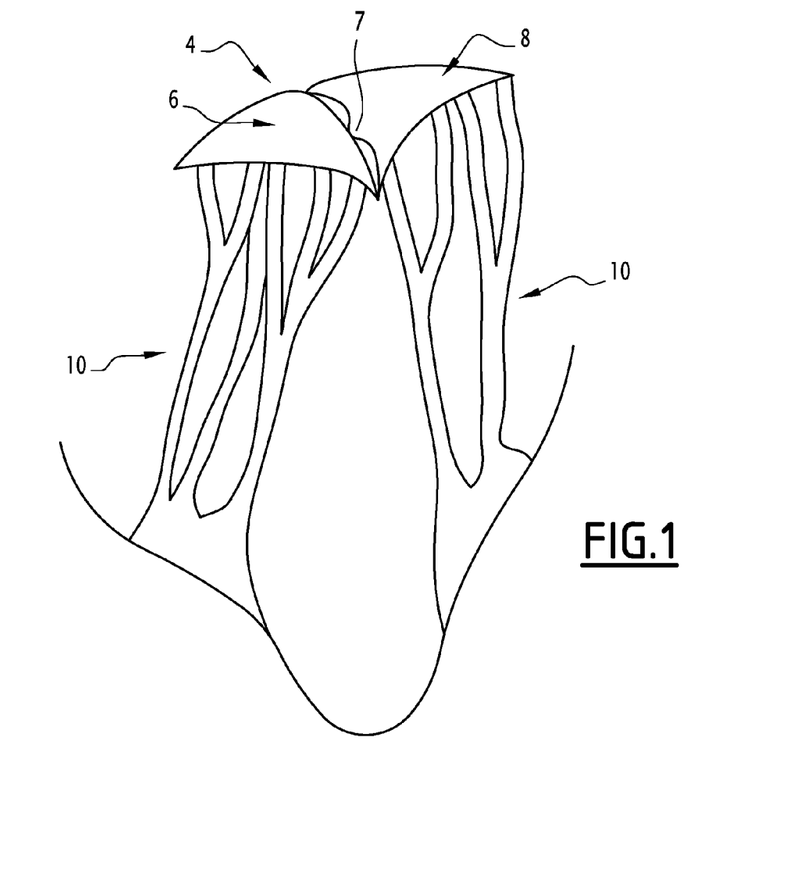
FIG. 1 is a schematic illustration of a heart valve having a prolapse.

Such a valve 4 is illustrated in FIG. 1. It is typically formed with an anterior leaflet 6 and a posterior leaflet 8. The prolapse 7 is located on the posterior leaflet 8. The leaflets of the valve 4 are connected to the wall of the left auricle via strings 10.

The prolapse forms a bulge which protrudes at the free edge of the leaflet 8 preventing coaptation between the free edges of the leaflets 6, 8 of the valve.

As illustrated in FIG. 4, the treatment kit 2 according to the invention comprises a treatment clamp 12 and a stent rod 14 extending along a main axis X and defining at least one distal aperture 16 for retaining the clamp 12.

Figure 2:
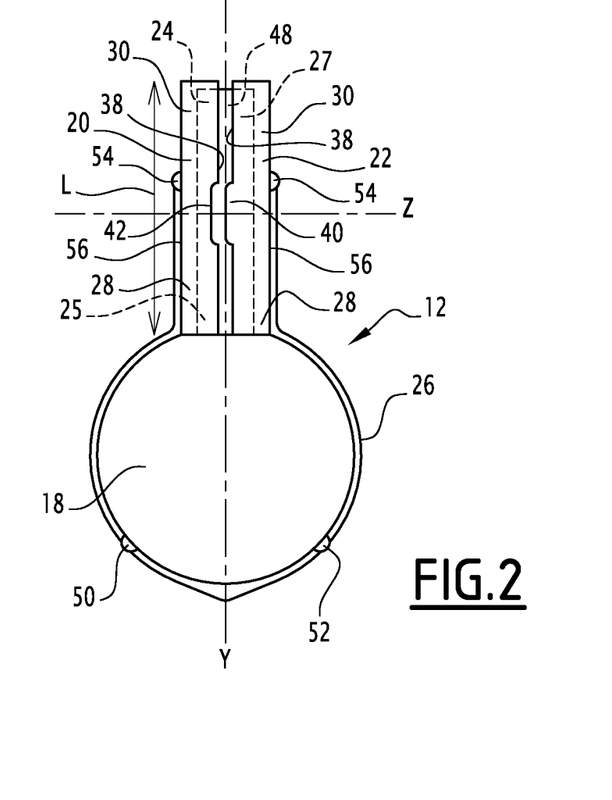
FIG. 2 is a schematic illustration of a clamp for treating a bodily tissue according to the invention.

As for the example visible in FIG. 2, the clamp 12 includes a basic body 18, a first flexible clamping arm 20, a second flexible clamping arm 22, and a flexible crushing member 24.

The clamp 12 further includes a member 26 for deforming the clamping arms 20, 22.

The body 18 includes in this example a substantially circular section. The diameter of the body 18 is advantageously comprised between 1 mm and 15 mm, notably comprised between 2 mm and 10 mm, and preferably equal to 8 mm. It is formed by a material such as metal or plastic.

The body 18 is advantageously maintained fixed in rotation with respect to the main axis X of the stent rod 14. For this purpose, at least one transverse section of the body 18 advantageously has a shape mating the inner cross-section of the stent rod 14 at the aperture 16.

Figure 3:
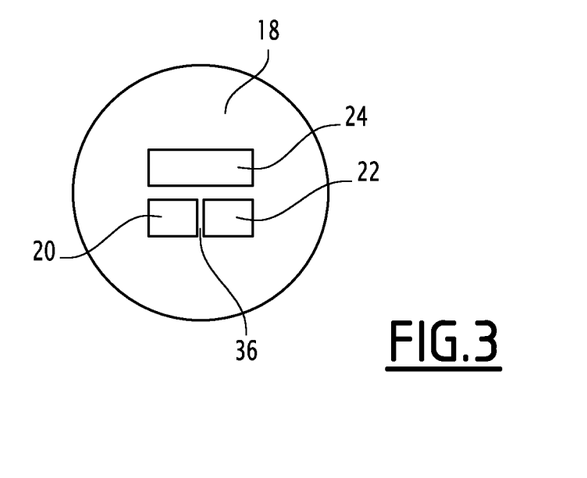
FIG. 3 is a front view of the treatment clamp according to the invention.

The first clamping arm 20 and the second clamping arm 22 protrude with respect to the body 18 along a longitudinal axis Y of the clamp. They each comprise a proximal end 28 bound to the body 18 and a free distal end 30 opposite to the proximal end 28. They delimit together an inner clamping area 36, visible in FIG. 3.

Figures 5, 6:
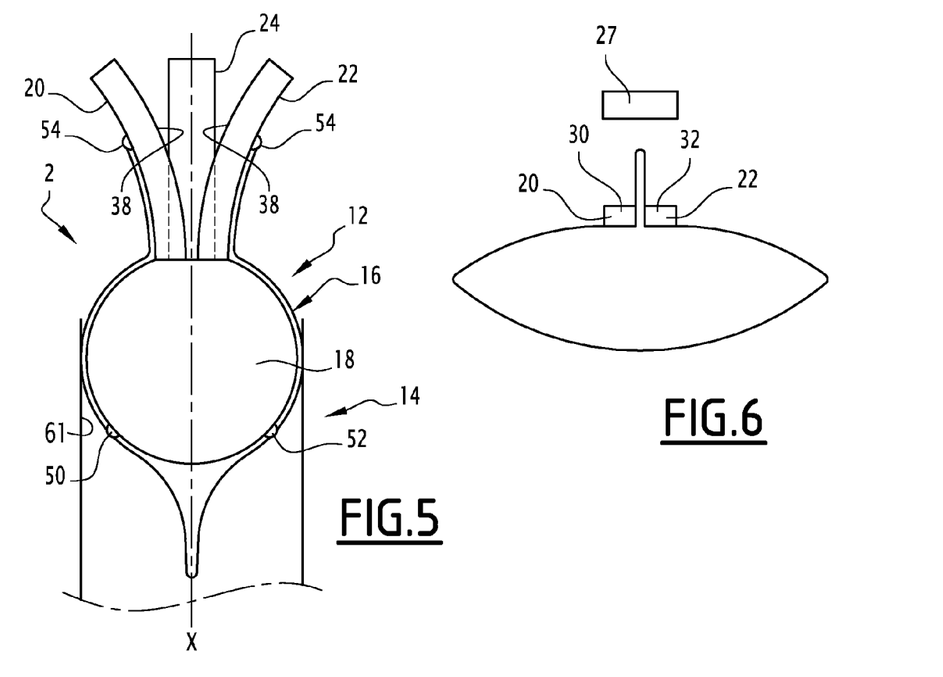
FIG. 5 is a schematic illustration of an operating step of the treatment clamp according to the invention.
FIG. 6 is a schematic illustration of a valve leaflet having a prolapse, clamped by the treatment clamp according to the invention.

The two clamping arms 20, 22 are deformable between a closed rest configuration, visible in FIG. 2, in which the distal ends 30 of both clamping arms 20, 22 are brought closer together, and an open separation configuration, visible in FIG. 5, in which the distal ends 30 of both clamping arms 20, 22 are spaced apart from each other.

Thus, in the closed rest configuration, both clamping arms 20, 22 extend facing each other and parallel to the longitudinal axis Y of the clamp 12.

Each clamping arm 20, 22 has a length L along the longitudinal axis Y of the clamp 12. The length of the first clamping arm 20 is substantially equal to the length of the second clamping arm 22. The length L of the first 20 and second 22 arms is advantageously comprised between 5 mm and 25 mm, in particular comprised between 8 mm and 15 mm and preferably equal to 10 mm.

Further, each clamping arm 20, 22 comprises a surface 38 for laterally clamping the prolapse.

The side clamping surface 38 of the first arm 20 extends facing the side clamping surface 38 of the second arm 22, on either side of the longitudinal axis Y.

In this example, each clamping surface 38 comprises at least one protruding portion 40 and at least one additional recessed portion 42, respectively.

For example and as illustrated in FIG. 2, the first clamping arm 20 comprises a side clamping surface 38 having a recess 42, and the second clamping arm 22 includes a side clamping surface 38 including a protruding portion 40 mating the recess 42.

Alternatively and as visible in FIG. 4, the side clamping surface 38 of the first arm 20 includes a plurality of teeth 44 and the side clamping surface 38 of the second arm 22 includes a plurality of teeth 46 mating the teeth 44 of the first arm 20.

Alternatively, the clamping surfaces 38 are smooth, as illustrated in FIG. 5.

The body 18, the first clamping arm 20 and the second clamping arm 22 are advantageously made in one piece and made together in the same material. For example they are made from a metal or plastic material.

The crushing member 24 protrudes from the body 18 facing the first and second clamping arms 20, 22 between an end 25 bound to the body 18 and a free end 27.

The crushing member 24 is for example formed with a blade 24 extending along the longitudinal axis Y of the clamp 12 and along a transverse axis Z perpendicular to the longitudinal axis Y. The crushing member 24 extends over a length substantially equal to the length L of the first and second clamping arms 20, 22.

Figure 7:
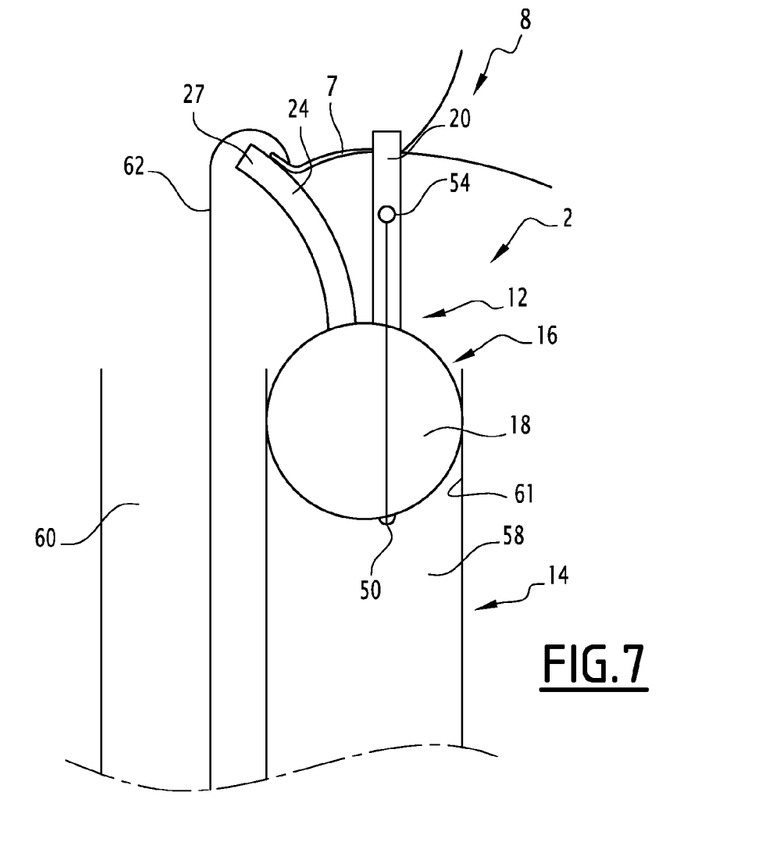
FIG. 7 is a schematic illustration of a subsequent operation step of the treatment kit according to the invention.
Figure 8:
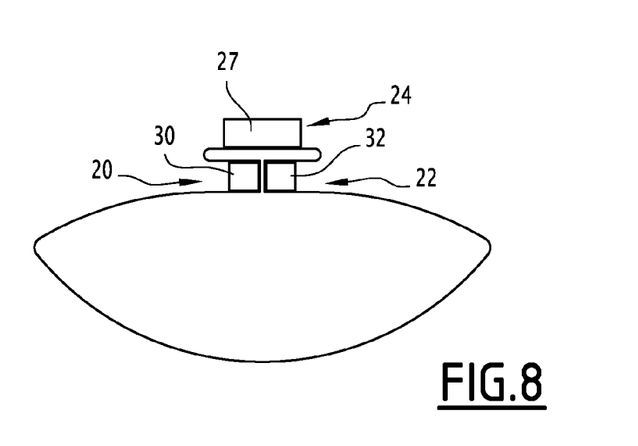
FIG. 8 is a schematic illustration of a valve leaflet having a prolapse, clamped and crushed by the treatment clamp according to the invention.

The crushing blade 24 is movable with respect to the clamping arms 20, 22 between a position for inserting the prolapse, visible in FIG. 7, separated from the clamping arms 20, 22, and a position for crushing the prolapse, visible in FIG. 8, moved closer to the arms 20, 22.

In the closer position, the crushing blade 24 extends parallel to the longitudinal axis Y of the clamp 12, facing the first arm 20 and the second clamping arm 22.

The clamping member 24 is advantageously elastically urged towards the closer position.

In the position for inserting the prolapse, the free end 27 of the crushing blade 24 is located transversely at a distance from the distal end 30 of the arms, away from the longitudinal axis Y, so as to allow insertion of the prolapse between the blade 24 and the arms 20, 22.

In the example of FIG. 7, the crushing blade 24 is curved away from the longitudinal axis Y by moving it from the bound end 25 to the free end 27.

Moreover, in the position for inserting the prolapse, the first clamping arm 20 is movable with respect to the second clamping arm 22, and conversely along a separation direction between the closed configuration and the open configuration.

According to a first embodiment and as visible in FIG. 7, the free end 27 of the crushing blade 24 is movable substantially perpendicularly with respect to each separation direction of the clamping arms 20, 22 between the insertion position and the crushing position.

Alternatively (not shown), the free end 27 of the crushing blade 24 is movable parallel to at least one separation direction between the insertion position and the crushing position.

Advantageously, the crushing blade 24 has an inner surface 48 for crushing the prolapse. The inner crushing surface 48 substantially extends perpendicularly to the side clamping surface 38 of each clamping arm 20, 22.

Advantageously, the crushing blade 24 is made in one piece with the body 18 and the arms 20, 22.

The deformation member 26 is formed with a wire 26 attached to a first end on the first clamping arm 20 and attached to a second end on the second clamping arm 22.

The wire 26 is further locally maintained against the body 18, for example in two guidance points 50, 52, for example formed with jumpers located on the circumference of the body 18 and at a distance from each other.

In the example of FIG. 2, the wire 26 is borne by the body 18 and partly extends along the circumference of the body 18.

The wire 26 is connected to each clamping arm 20, 22 in an attachment point 54. The attachment points 54 are located on the first arm 20 and the second arm 22, respectively, between the proximal end 28 and the distal end 30 of each arm 20, 22. The attachment points 54 are advantageously located on a face 56 of each arm 20, 22 opposite to the side clamping surface 38.

The wire 26 is engaged through each guidance point 50, 52 in order to freely slide in the guidance point 50, 52.

The wire 26 may be actuated in order to deform both clamping arms 20, 22 between the closed rest configuration and the open separation configuration. This actuation is advantageously performed by traction on the proximal end of the wire 26 located between both guidance points 50, 52, opposite to the clamping arms 20, 22.

The wire 26 is advantageously formed with a material such as a biocompatible wire, either in fabric, for example in polyester, on in metal, for example in stainless steel or in Nitinol.

In the example illustrated in FIG. 7, the stent rod 14 includes a first side compartment 58 and a second side compartment 60.

The first compartment 58 is intended to accommodate the clamp 12. It comprises an internal maintaining surface 61 able to maintain the body 18 fixed in rotation with respect to the main axis X of the stent rod 14.

The second compartment 60 is intended to accommodate a member for capturing the prolapse and for actuating the crushing member which, in this example is a movable hook 62 with respect to the stent rod 14.

The movable hook 62 is intended to maneuver the crushing blade 24 between the position for inserting the prolapse and the position for crushing the prolapse.

The movable hook 62 is advantageously freely mounted so as to slide inside the second compartment 60 of the stent rod 14.

The operation of the treatment kit 2 according to the invention, during the treatment of a prolapse of a mitral valve, will now be described, with reference to FIGS. 4 to 8.

Initially, the treatment kit 2 is provided. In the first compartment 58, the clamp 12 is accommodated in the stent rod 14. The body 18 is maintained fixed in rotation relatively to the main axis X of the stent rod 14. The movable hook 62 is retracted in the second compartment 60.

The body 18 is thus partly engaged into the stent rod 14. The arms 20, 22 and the crushing member 24 protrude axially out of the stent rod 14.

An external sheath (not shown) exteriorly covers the stent rod 14 and the portion of the clamp 12 which protrudes axially out of the stent rod 14.

Next, the treatment kit 2 is brought to the mitral valve to be treated, via an endovascular route, i.e. by introduction into the femoral vein ranged up to the right auricle, and passing through the left auricle via a transseptal route.

The external sheath is then moved relatively to the stent rod 14 in order to uncover the portion of the clamp 12 axially protruding out of the stent rod 14.

As illustrated by FIG. 4, the first clamping arm 20 and the second clamping arm 22 then occupy the rest configuration and the crushing blade 24 occupies the closed position.

The prolapse is then captured at its free end by means of the hook 62. The operator properly positions and then actuates the deformation member 26 so as to deform the clamping arms 20, 22 towards the open separation configuration. More specifically, the operator exerts traction on the wire 26 in the direction opposite to the clamping arms 20, 22, in the proximal portion of the wire 26 located between both guidance points 50 52, at equal distance between both guidance points 50, 52. The stent rod 14 axially retains the body 18.

The clamping arms 20, 22 are then separated from each other and able to receive the prolapse in the clamping area 36.

Next, the operator will hook up the free end 27 of the crushing blade 24 by means of the movable hook 62, so as to deform the crushing blade 24 towards the position for inserting the prolapse, separated from the clamping arms 20, 22, as illustrated in FIG. 7.

Next, the operator positions the distal ends 30 of the clamping arms 20, 22 on either side of the prolapse, by pulling the free edge of the leaflet 8 in order to bring the prolapse between the side clamping surfaces 38 by means of a movable hook 62.

Next, when the prolapse is accommodated along the axis Y between the side clamping surfaces 38, and under the crushing blade 24, the operator releases the deformation wire 26. This causes deformation of the clamping arms 20, 22 towards the rest configuration, so that the distal ends 30 of the clamping arms 20, 22 are brought closer in order to clamp the prolapse between the side clamping surfaces 38, as illustrated in FIG. 6.

Next, the operator releases the movable hook 62. The crushing blade 24 deforms then spontaneously towards the position for crushing the prolapse brought closer to the clamping arms 20, 22, so as to crush the upper portion of the prolapse protruding beyond the arms 20, 22, towards the arms 20, 22 as illustrated in FIG. 8.

The prolapse then has a cross-section substantially with the shape of an omega.

The distal ends 30 of the arms 20, 22 are then located in the vicinity of the free edge of the leaflet 8, the body 18 being placed facing the leaflet 8 interiorly relatively to the free end.

Finally, the operator withdraws the stent rod 14 and the movable hook 62. The clamp 12 remains attached on the leaflet 8 by crushing the prolapse.

Subsequently, coaptation between the free edges of the leaflets 6, 8 is re-established when the valve closes. However, the clamp 12 is displaceable together with the leaflet 8, independently of the leaflet 6, so that the valve normally opens without affecting the section of the aperture for the passing of the blood.

Thus it is conceivable that the treatment kit according to the invention treats a prolapse of a mitral valve in a particularly easy way and with less risks for the patient than an invasive operation.

Further, the treatment kit according to the invention effectively treats the prolapse. Indeed, once the prolapse has been crushed with the clamp according to the invention, the mitral valve may sealably close and coaptation of the posterior and anterior leaflets of the valve is ensured, while ensuring a section for letting through the blood as efficiently as possible when the valve is open.

The clamp according to the invention moreover more generally applies to the treatment of a prolapse on other tissues, such as the aortic valve and the tricuspid valve.

The capture member formed by the hook 62 and the displacement assembly formed by the flexible blade 24 forming a mechanism 100 for capturing and displacing the prolapse 7, able to bring the prolapse 7 between side clamping surfaces of the clamping arms and able to lift the prolapse 7 transversely at a distance from the distal ends of the clamping arms 20, 22 away from the longitudinal axis Y of the clamp 12.

The deformation of the crushing blade 24 along a displacement substantially perpendicular with respect to each separation direction of the clamping arms 20, 22 displaces the free end 27 of the crushing blade 24, and the movable hook 62 which has captured the prolapse 7 at a distance from the distal ends 30 of the arms, transversely away from the longitudinal axis Y, so as to insert the prolapse between the blade 24 and the arms 20, 22.

This greatly simplifies the insertion of the prolapse 7 into the clamp 12, by a simple and guided manipulation for the surgeon.

An alternative kit 2 according to the invention is illustrated with FIGS. 9 to 12.

The kit 2 illustrated in these figures differs from the one illustrated in FIGS. 1 to 8 in that the clamp 12 is not necessarily provided with a flexible crushing member 24.

Figure 9:
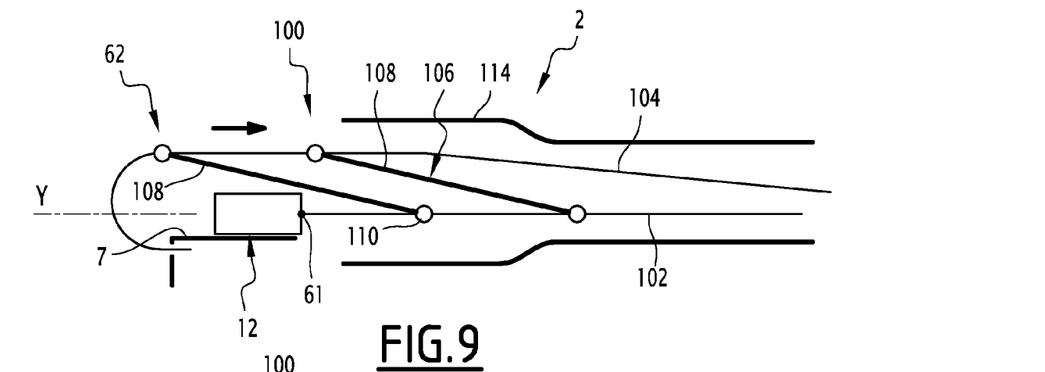
FIGS. 9 to 12 illustrate an alternative kit according to the invention.

In this embodiment, the kit 2 includes an elongated member 102 for retaining the clamp 12, positioned in the stent rod 14 for defining the surface 61 for maintaining it at its distal end.

The capture member 62 includes a hook at its distal end, and a proximal rod 104, inserted into the stent rod 14, and extending as far as the proximal end of the stent rod so as to be maneuvered by the surgeon.

Figure 10:
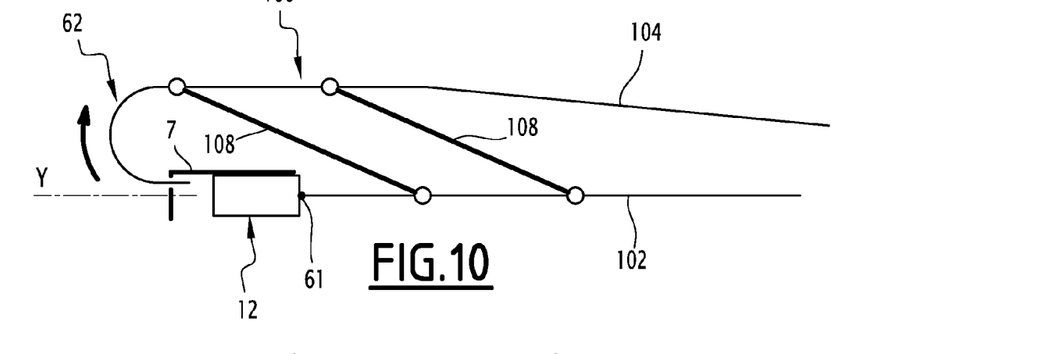

In addition to the capture member 62, the capture and displacement mechanism 100 includes an assembly for displacing 106 the capture member 62 and the prolapse 7, able to lift the capture member 62 from a distal position for capturing the free edge of the prolapse 7, illustrated by FIG. 9, to a proximal position for inserting and lifting the prolapse between the arms 20, 22 of the clamp 12, as illustrated with FIG. 10.

In this example, the displacement assembly 106 includes at least one jointed connecting rod 108 between the capture member 62 and the elongated member 102.

Figure 11:
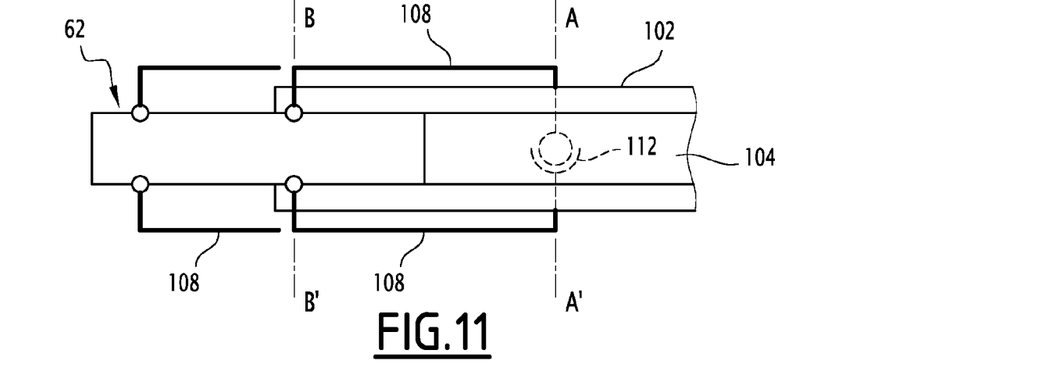

As illustrated by FIG. 11, the displacement assembly 106 advantageously includes at least one pair of connecting stent rods 108 mounted parallel to each other on either side of the capture member 62 and of the elongated member 102, and preferably as illustrated in FIG. 9, at least two pairs of connecting rods 108 spaced out along the elongated member 102 forming a jointing parallelogram.

Each connecting rod 108 is jointed in a first end 110 on the elongated member 102, in a proximal way relatively to the clamp 12, around at least one axis A-A' perpendicular to the axis Y of the clamp 12.

Figure 12:
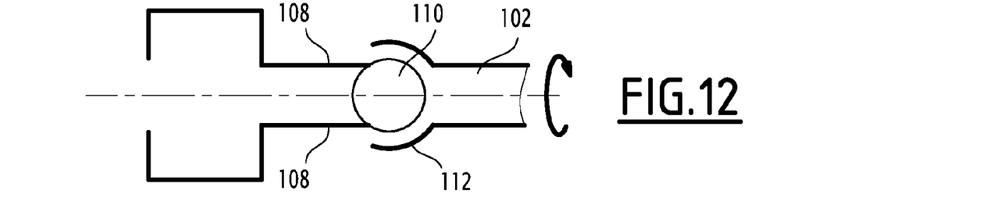

Preferably, as illustrated by FIG. 12, a ball-joint connection 112 is provided at the first end 110 for further allowing rotation of each connecting rod 108 and of the capture member 62 around the axis Y.

With reference to FIG. 11, each connecting rod 108 is further jointed on the capture member 62 around an axis B-B' parallel to the axis A-A', located in a distal way relatively to the axis A-A'.

In the distal portion visible in FIG. 9, the free end of the capture member 62 is axially located along the Y axis in a distal way relatively to the free ends 30 of the clamping arms 20, 22. The connecting rods 108 are brought closer to the axis Y of the clamp 12.

In the proximal position visible in FIG. 10, the free end of the capture member 62 is axially brought closer to the clamp 12 along the axis Y, so as to be advantageously located axially facing the clamp 12.

The connecting rods 108 are moved away from the axis Y of the clamp 12 and have lifted the free end of the capture member 62 and the prolapse 7 above the clamp 12, by moving them transversely at a distance from the distal ends 30 of the arms 20, 22, away from the longitudinal axis Y, as illustrated in FIG. 10.

The operation of the kit 2 illustrated in FIGS. 9 to 12 will now be described.

Initially, the clamp 12 is loaded into the elongated member 102 and is positioned in the stent rod 14. The capture member 62 occupies its distal position, with its free end at the front of the clamp 12. The stent rod 14 caps the clamp 12, the capture member 62 and the displacement assembly 106, advantageously in an end capsule 114.

The stent rod 14 is then introduced into the body of the patient and is brought as far as the localization of the prolapse 7. The surgeon then discovers the clamp 12, the capture member 62 and the displacement assembly 106, by partly withdrawing the stent rod 14.

Next, he/she captures the free edge of the prolapse 7 by means of the free hook-shaped end of the capture member 62. He/she pulls on the proximal rod 104 of the capture member 62, in order to have the capture member 62 pass from its distal position to its proximal position, while maintaining the elongated member 102 in position.

During this displacement, the connecting rods 108 pivot around their axes A-A' and B-B'. They gradually move away from the axis Y, causing gradual lifting and simultaneous traction of the prolapse 7 between the arms 20, 22 of the clamp 12.

The surgeon then closes the arms 20, 22 of the clamp 12 towards the rest configuration for clamping the prolapse 7 between the side clamping surfaces 38, as described earlier.

Optionally, the surgeon pivots the capture member 62 and the connecting rods 108 around the axis Y for disengagement from the prolapse 7.

Next, the surgeon releases the clamp 12 and withdraws the elongated member 102 and the capture member 62 by axial displacement.

The kit 2 described in these figures, is therefore particularly simple and accurate to use.

Another alternative kit 2 according to the invention is illustrated by FIGS. 13 to 17.

Figure 13:
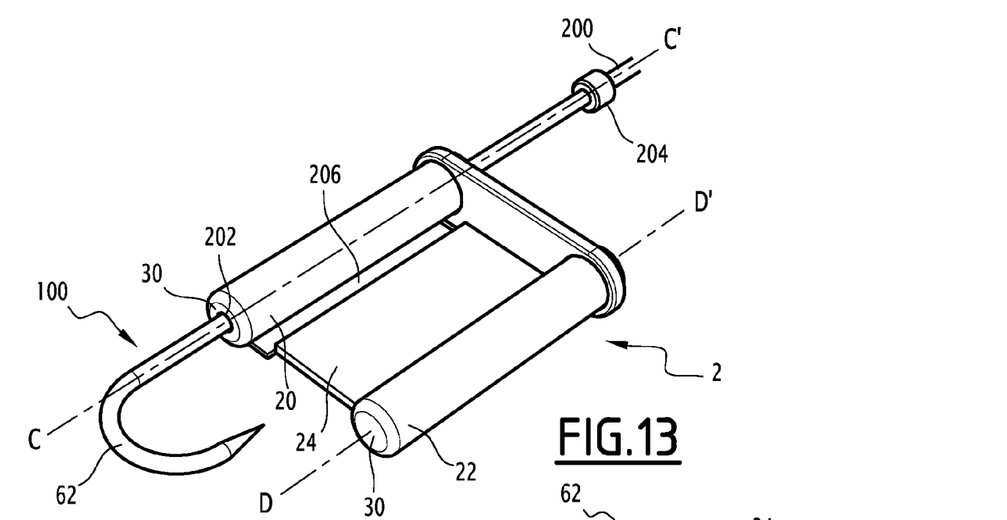
FIGS. 13 to 17 illustrate another alternative kit according to the invention.

In this alternative, the capture and displacement mechanism 100 includes, in addition to the capture member 62, an assembly for displacing the capture member 62 comprising a proximal link 200 for manipulating the capture member 62 is a passage 202 for guiding in rotation and in translation the capture member 62.

The proximal link for manipulation 200 has a distal end removably mounted on the proximal end of the capture member 62 and a proximal end able to be manipulated by the operator of the kit 2.

A connector 204 which may for example be disassembled by screwing ensures the connection between the proximal link for manipulation 200 and the capture member 62.

In this example, the guide passage 202 is made in one of the arms 20 of the clamp 12, along an axis C-C' of the arm 20.

The arms 20, 22 are rigid here.

Figure 14:
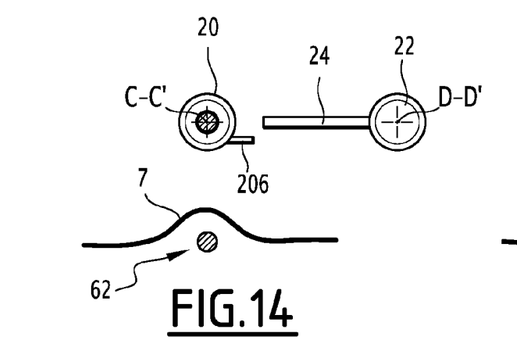
Figure 15:
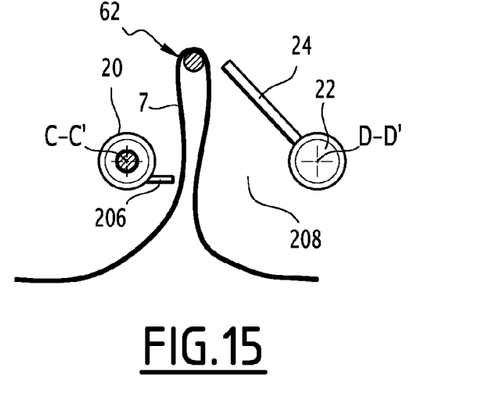

The capture member 62 is rotatably mounted around the axis C-C' in the guide passage 202 between a lower configuration for capturing an edge of the prolapse 7, visible in FIG. 13 and in FIG. 14 and an upper configuration for lifting the prolapse transversely with respect to the axis C-C', visible in FIG. 15, for bringing it between the arms 20, 22.

The capture member 62 is further mounted so as to be translationally movable along the axis C-C' between a distal position in which its distal hook-shaped end and located at the front of the distal end 30 of each arm 20, 22, and a proximal position in which its distal hook-shaped end is located between the arms 20, 22.

Advantageously, the clamp 12 further includes a member 24 for crushing the prolapse 7, borne by a second arm 22, and an abutment 206 for retaining the crushing member 24, borne by the first arm 20.

The crushing member 24 is formed here by a plate for crushing the prolapse.

Figure 16:
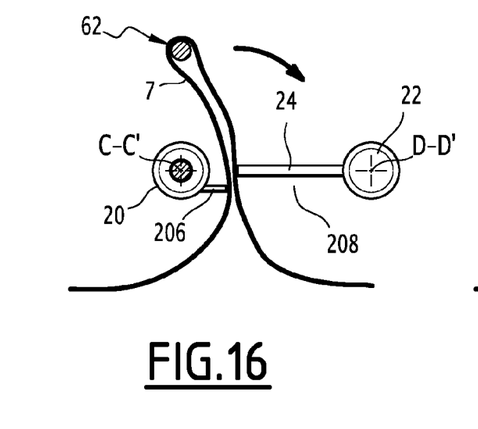
Figure 17:
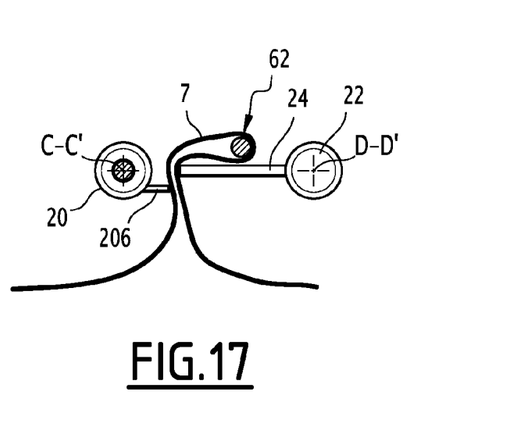

The crushing member 24 is more generally movable between an open position for introducing the prolapse 7 between the arms 20, 22, visible in FIG. 15, and a closed position for blocking the prolapse 7, visible in FIGS. 16 and 17.

Preferably, the crushing member 24 is rotatably mounted around the axis D-D' of the second arm 22, for example by being attached to a rotary sleeve around the second arm 22, or by being attached to the second arm 22, the second arm 22 being rotatable around its axis.

In the open position, visible in FIG. 15, the crushing member 24 has been lifted away from the intermediate space 208 defined between the arms. It protrudes above the arms 20, 22. The insertion of the prolapse 7 between the arms 20, 22 is possible.

In the closed position, visible in FIG. 16 or in FIG. 17, the crushing member 24 is positioned transversely between the arms 20, 22. It is applied on the abutment 206.

The operation of the kit 2 described in FIGS. 13 to 17 will now be described.

Initially, the clamp 12 is brought facing a leaflet of the native valve, in the vicinity of the prolapse.

The capture member 62 is placed in its lower configuration for capturing the prolapse, and in its distal position, as illustrated by FIG. 14.

The clamp 12 is moved backwards in order to capture the free end of the prolapse 7 at the hook defined at the free end of the capture member 62.

Next, the proximal link 200 is maneuvered by the operator for pivoting the capture member 62 in a first direction following a rotation advantageously greater than or equal to 180° around the axis C-C' in the passage 202, by driving the free edge of the prolapse 7.

During this movement, the crushing member 24 is able to be maneuvered in order to pass into its open position.

This pivoting of the capture member 62, advantageously associated with a translational displacement between the distal position and the proximal position, inserts the prolapse 7 between the arms 20, 22 and simultaneously lifts the prolapse 7 above the arms 20, 22 by moving it away transversely from the axis C-C', D-D' of each arm 20, 22, as illustrated by FIG. 15.

Next, the crushing member 24 returns to its closed position by clamping the prolapse 7 at its base, as illustrated by FIG. 16.

Next, the operator again pivots the capture member 62 in a second direction opposite to the first direction, in order to apply the protruding portion of the prolapse 7 against the crushing member 24.

He/she then releases the maneuvering link 200 by disconnecting the connector 204 and by leaving in place or permanently the capture member 62.

In an alternative (not shown), the capture member 62 is rotatably mounted in a passage 202 located under the arm 20 and not in the arm 20.

In another alternative (not shown), the capture member 62 is withdrawn out of the body of the patient, after crushing the prolapse 7.

Figure 18:
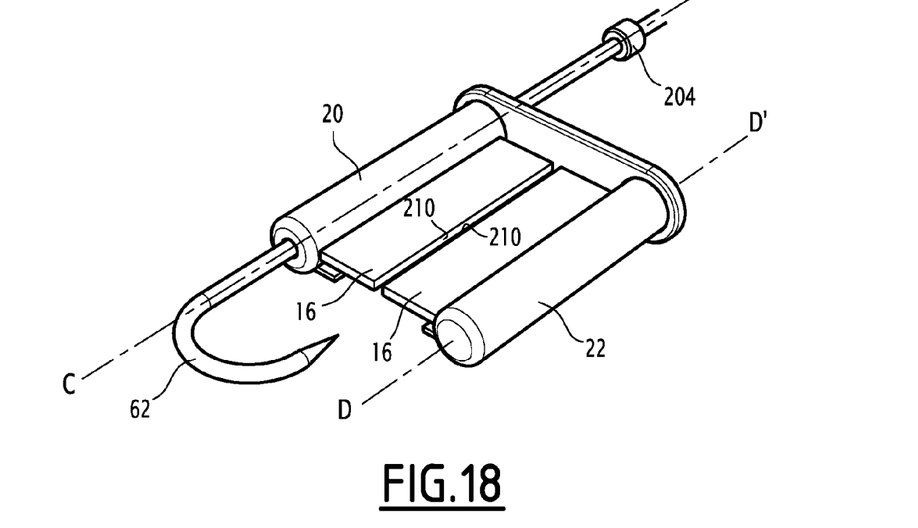
FIG. 18 illustrates another alternative kit according to the invention.

In the alternative illustrated in FIG. 18, each arm 20, 22 is provided with a specific crushing member 16, movable between the open position and the closed position.

The prolapse 7 is clamped between the free edges 210 of the crushing members 16 in their closed position.

Figure 19:
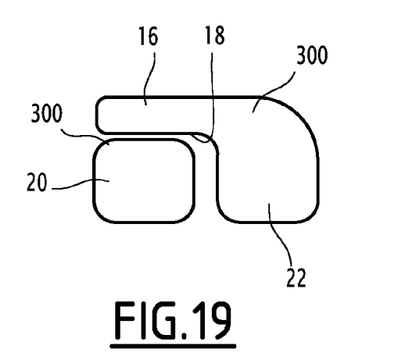
FIGS. 19 to 21 illustrate other alternative kits according to the invention.
Figure 20:
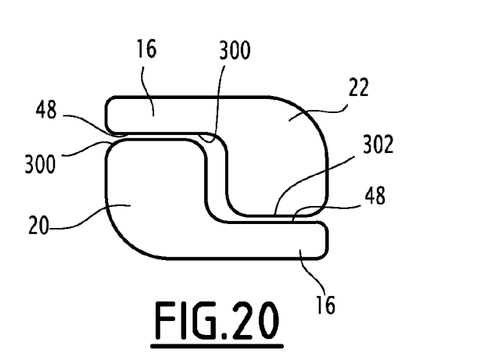
Figure 21:
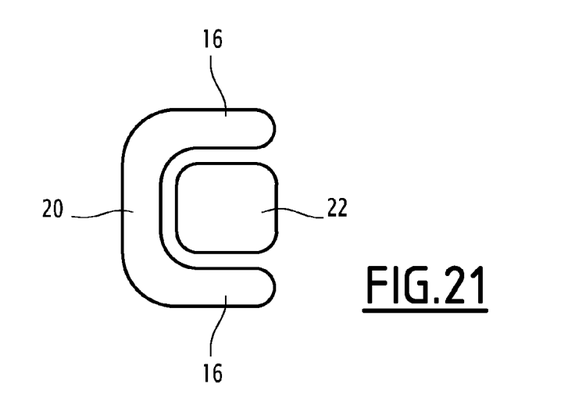

In the alternatives of FIGS. 19 to 21, the crushing member 16 is provided, secured and displaceable together with at least one of the arms 20, 22.

In FIG. 19, a crushing member 16 protrudes transversely with respect to the axis of the second arm 22 towards the first arm 20.

It preferably extends along an upper surface 300 of the second arm 22. It defines an interior crushing surface 48 able to be applied on an upper surface of the first arm 20.

In the alternative of FIG. 20, the first arm 20 is also provided with a crushing member 16 which protrudes transversely with respect to the axis of the first arm 20 from a lower surface 302 of the first arm 20.

It defines a crushing surface 48 able to be applied under a lower surface 302 of the second arm.

In the alternative illustrated by FIG. 21, the first arm 20 is provided with two opposite crushing members 16 defining between them a housing for inserting the second arm 22.

The invention claimed is:

1. A kit for treating a bodily tissue having a prolapse, comprising:
   a treatment clamp, comprising:
      a body; and
      at least two arms protruding with respect to the body, each arm comprising a proximal end connected to the body and a free distal end opposite to the proximal end, and
   a capture and displacement mechanism adapted to capture and displace the prolapse with respect to the treatment clamp, the capture and displacement mechanism being configured to insert the prolapse between side surfaces of the arms, and comprising:
      a free end capture member adapted to capture the prolapse at its free end; and
      a displacement assembly displacing the capture member with respect to the arms,
   wherein the capture member is engaged through a guidance passage made in one of the arms or positioned under one of the arms and is mounted so as to be displaceable in translation and in rotation in the guidance passage.

2. The kit according to claim 1, wherein the capture and displacement mechanism is configured to lift the prolapse at a distance from the distal ends of the arms, transversely away from the longitudinal axis of the treatment clamp.

3. The kit according to claim 1, wherein the treatment clamp includes at least one member for crushing the prolapse, rotatably mounted around the axis of one or both arms, between an open position for inserting the prolapse between the arms and a closed position for clasping the prolapse.

4. The kit according to claim 3, wherein the treatment clamp includes at least one abutment for retaining the crushing member in the closed position.

5. The kit according to claim 1, further comprising a retaining member adapted to retain the treatment clamp during the insertion of the prolapse,
   wherein the displacement assembly adapted to displace the capture member being jointed on the retaining member and on the capture member, the displacement assembly being configured to displace a free end of the capture member from a distal position capturing the prolapse located in a distal way with respect to the distal end of the arms, towards a proximal lifted position for inserting the prolapse axially located facing and transversely away from a longitudinal axis of the treatment clamp.

6. The kit according claim 5, wherein the clamp comprises two arms and both arms are flexible clamping arms, deformable between a closed rest configuration in which the distal ends of both arms are brought closer to each other, and an open separation configuration in which the distal ends of both arms are spaced apart from each other.

7. The kit according to claim 6, wherein the displacement assembly includes at least one flexible member for crushing the prolapse, the crushing member protruding from the body facing the arms between an end bound to the body and a free end,
   the crushing member being movable with respect to the arms between a position for inserting the prolapse away from the arms and a closer position for crushing the prolapse to the arms, and
   wherein each arm is movable with respect to the other arm along a separation direction between the closed configuration and the open configuration, the free end of the crushing member being movable substantially perpendicularly with respect to each separation direction between the insertion position and the crushing position or being movable parallel to at least one separation direction between the insertion position and the crushing position.

8. The kit according to claim 6, wherein the treatment clamp comprises a deforming member deforming the arms borne by the body, the member for deforming the arms being connected to both arms and being able to be actuated for deforming both arms between the closed rest configuration and the open separation configuration.

9. The kit according to claim 8, wherein the deforming member comprises a wire connected to both arms, the wire being maintained with respect to the body in at least one guidance point.

10. The kit according to claim 9, wherein the wire extends partly along the circumference of the body.

11. The kit according to claim 6, wherein each arm comprises a side clamping surface for the prolapse, each clamping surface extending facing each other and comprising at least one additional protruding portion and at least one additional recessed portion, respectively.

12. The kit according to claim 11, wherein the displacement assembly includes at least one flexible member adapted to crush the prolapse, the crushing member protruding from the body facing the arms between an end bound to the body and a free end,
    wherein the crushing member is movable with respect to the arms between a position for inserting the prolapse away from the arms and a closer position for crushing the prolapse to the arms, and
    wherein the crushing member comprises an internal surface adapted to crush the prolapse substantially extending perpendicularly to the side clamping surface of each arm.

13. The kit according to claim 1, wherein the displacement assembly comprises at least one flexible member adapted to crush the prolapse, the crushing member protruding from the body facing the arms between an end bound to the body and a free end and being movable with respect to the arms between a position for inserting the prolapse away from the arms and a closer position for crushing the prolapse to the arms.

14. The kit according to claim 13, wherein the crushing member is elastically urged towards the closer position.

15. The kit according to claim 13, wherein the body, both arms and the crushing member are made in one piece and made together in the same material.

16. The kit according to claim 1, further comprising a stent rod extending along a main axis and defining at least one aperture retaining the treatment clamp.

17. The kit according to claim 16, wherein the stent rod comprises a first compartment and a second compartment, the first and second compartments extending along the main axis, the first compartment containing the treatment clamp, the second compartment containing at least partly the mechanism for capturing and displacing the prolapse.

18. The kit according to claim 1, wherein the free end capture member is a hook.

19. A kit for treating a bodily tissue having a prolapse, comprising:
    a treatment clamp, comprising:
        a body; and
        at least two arms protruding with respect to the body, each arm comprising a proximal end connected to the body and a free distal end opposite to the proximal end;
    a capture and displacement mechanism adapted to capture and displace the prolapse with respect to the treatment clamp, the capture and displacement mechanism being configured to insert the prolapse between side surfaces of the arms, and comprising:
        a free end capture member adapted to capture the prolapse at its free end; and
        a displacement assembly displacing the capture member with respect to the arms; and
    a retaining member adapted to retain the treatment clamp during the insertion of the prolapse,
    wherein the displacement assembly is jointed on the retaining member and on the capture member, the displacement assembly being configured to displace a free end of the capture member from a distal position capturing the prolapse located in a distal way with respect to the distal end of the arms, towards a proximal lifted position for inserting the prolapse axially located facing and transversely away from a longitudinal axis of the treatment clamp.

20. A kit for treating a bodily tissue having a prolapse, comprising:
    a treatment clamp, comprising:
        a body; and
        at least two arms protruding with respect to the body, each arm comprising a proximal end connected to the body and a free distal end opposite to the proximal end, and
    a capture and displacement mechanism adapted to capture and displace the prolapse with respect to the treatment clamp, the capture and displacement mechanism being configured to insert the prolapse between side surfaces of the arms, and comprising:
    a free end capture member adapted to capture the prolapse at its free end; and
    a displacement assembly displacing the capture member with respect to the arms, and comprising at least one flexible member adapted to crush the prolapse, the flexible member protruding from the body facing the arms between an end bound to the body and a free end and being movable with respect to the arms between a position for inserting the prolapse away from the arms and a closer position for crushing the prolapse to the arms.

* * * * *